US00PP24570P3

(12) United States Plant Patent
Leis et al.

(10) Patent No.: US PP24,570 P3
(45) Date of Patent: Jun. 24, 2014

(54) APPLE TREE NAMED 'RENOIRCIV'

(50) Latin Name: *Malus domestica Mill.*
Varietal Denomination: RENOIRCIV

(75) Inventors: Michelangelo Leis, Ferrara (IT); Alessio Martinelli, Ferrara (IT); Francesco Tagliani, Argenta (IT); Gianfranco Castagnoli, Quingentole (IT); Donata Azzolini, legal representative, Quingentole (IT); Pietro Castagnoli, legal representative, Quingentole (IT); Alessandro Castagnoli, legal representative, Quingentole (IT)

(73) Assignee: C.I.V.—Consorzio Italiano Vivaisti—Società Consortile A R.L., Comacchio FE (IT)

( * ) Notice: Subject to any disclaimer, the term of this patent is extended or adjusted under 35 U.S.C. 154(b) by 76 days.

(21) Appl. No.: 13/385,525

(22) Filed: Feb. 24, 2012

(65) Prior Publication Data

US 2013/0031686 P1 Jan. 31, 2013

(30) Foreign Application Priority Data

Jul. 26, 2011 (QZ) ..... PBR 2011/1877

(51) Int. Cl.
*A01H 5/00* (2006.01)

(52) U.S. Cl.
USPC ..... Plt./161

(58) Field of Classification Search
USPC ..... Plt./161
See application file for complete search history.

(56) References Cited

PUBLICATIONS

Jankovic, P. "Sweet Resistance," Fruit, Review for Fruit Growing, Viticulture, and Enology, vol. No. 12, Issue No. XXI, Dec. 2010, pp. 9-10 (translation provided).*

* cited by examiner

*Primary Examiner* — Susan McCormick Ewoldt
(74) *Attorney, Agent, or Firm* — Foley & Lardner LLP

(57) ABSTRACT

A new and distinct *Malus domestica Mill.* apple tree variety named 'RENOIRCIV' particularly characterized by moderately vigorous tree with good habit and good productivity. Resistant to scab. The tree produces well on two-year-old branches, is self-thinning and naturally keeps to one or two apples per cluster. The shape of fruit is conical-obloid, slightly flattened. Yellowish-green ground color with russeting over 50-60% of the surface; fruit growing in direct sunlight may take on a light red hue on the exposed part. The flavor is excellent with a very intense aroma similar to 'Reinette blanche du Canada', but sweeter. The fruit is good to eat fresh, even directly after harvest. The flesh is yellow, firm and juicy. May be stored until April.

4 Drawing Sheets

Latin name of the genus and species of the plant claimed: *Malus domestica Mill.*

Variety denomination: 'RENOIRCIV'.

PRIORITY CLAIM

This application claims priority to European Community Plant Variety Office Application No. 2011/1877, filed Jul. 26, 2011.

BACKGROUND OF THE INVENTION

The present invention relates to a new and distinct variety of apple tree, botanically known as *Malus domestica Mill.* of the Family Rosaceae, and hereinafter referred to by the variety denomination 'RENOIRCIV'.

The new *Malus* variety is a product of a planned breeding program conducted by the inventors, Michelangelo Leis, Alessio Martinelli, Gianfranco Castagnoli and Francesco Tagliani in S. Giuseppe di Comacchio (Ferrara), Italy. The objective of the breeding program was to develop new *Malus* varieties with improved production characteristics, high-quality flavour and aroma, and sustainability by increasing the tree's natural resistance. The primary objective of the research programme is to select new apple varieties with natural resistances, in particular to scab.

The new *Malus* variety, 'RENOIRCIV', originated from a cross made in a planned, controlled breeding program in S. Giuseppe di Comacchio (Ferrara), Italy. The female parent is an unpatented proprietary selection denominated 'FG-88'. The male parent is an unpatented proprietary selection denominated 'B9-5'. 'RENOIRCIV' was discovered and selected in August 2004 by the inventors as a flowering plant within the progeny of the stated cross in a controlled environment in S. Giuseppe di Comacchio (Ferrara), Italy.

Asexual reproduction of the new *Malus* variety by budding and grafting was first performed in September 2004 and in the following years in S. Giuseppe di Comacchio (Ferrara), Italy, and has demonstrated that the combination of characteristics as herein disclosed for the new *Malus* variety are firmly fixed and retained through successive generations of asexual reproduction. The new variety reproduces true to type.

BRIEF DESCRIPTION OF THE INVENTION

The following traits have been repeatedly observed and are determined to be unique characteristics of 'RENOIRCIV' which in combination distinguish this apple tree as a new and distinct variety:

1. Yellowish-green colour with russeting over 50-60% of the surface;
2. Scab resistance;
3. Medium vigor, open habit with short branches;
4. Self-thinning and naturally keeps to one or two apples per cluster;
5. The fruit is good to eat fresh, even directly after harvest;
6. High sugar content and
7. Long storage ability.

Of the commercial cultivars known to the inventors, the most similar in comparison to 'RENOIRCIV' is the variety 'Reinette blanche du Canada' (unpatented). In comparison to the similar variety 'Reinette blanche du Canada', 'RENOIRCIV' differs primarily in the traits listed in Table 1:

TABLE 1

| Comparison with similar variety | | | |
|---|---|---|---|
| Denomination of similar variety | Characteristic in which the similar variety is different | State of expression of similar variety | State of expression of candidate variety |
| "Reinette blanche du Canada" | General Shape | Obloid | Conic |
| | Eating maturity | Late | Medium |
| | Resistance to disease | No | Scab resistant |

In comparison to the parent varieties 'FG-88' and 'B9-5', 'RENOIRCIV' differs primarily in the traits listed in Table 2:

TABLE 2

| Comparison with parent varieties | | | |
|---|---|---|---|
| Characteristic in which the variety is different | State of expression of candidate variety | State of expression of female parent variety 'FG-88' | State of expression of male parent variety 'B9-5' |
| Resistance to Scab | Yes | No | Yes |
| Fruit over color | Absent or very small | Red | Yellow |
| Fruit Shape | Conic | Globose | Oviod |
| Area of russet on cheeks around the stalk | Very large; over 50-60% of the surface | Absent or small | Present around lenticels |
| Eating maturity | Medium | Medium | Very late |

BRIEF DESCRIPTION OF THE DRAWINGS

The accompanying photographs illustrate the overall appearance of the new apple tree 'RENOIRCIV' showing the colors as true as is reasonably possible with color reproductions of this type. Color in the photographs may differ slightly from the color value cited in the detailed botanical description, which accurately describe the color of 'RENOIRCIV'. In the photographs the label shows the breeder's reference 'B3B9-207'.

DETAILED BOTANICAL DESCRIPTION

Figure 1:
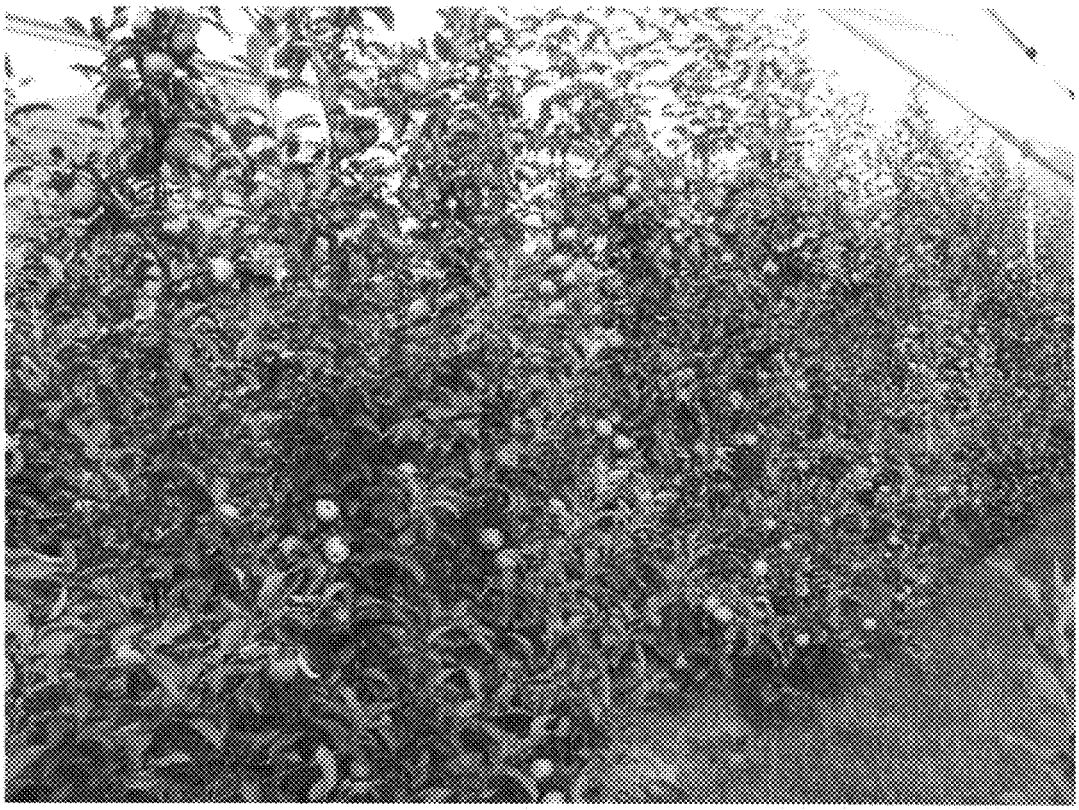
FIG. 1: illustrates the plant of 'RENOIRCIV'.
Figure 2:
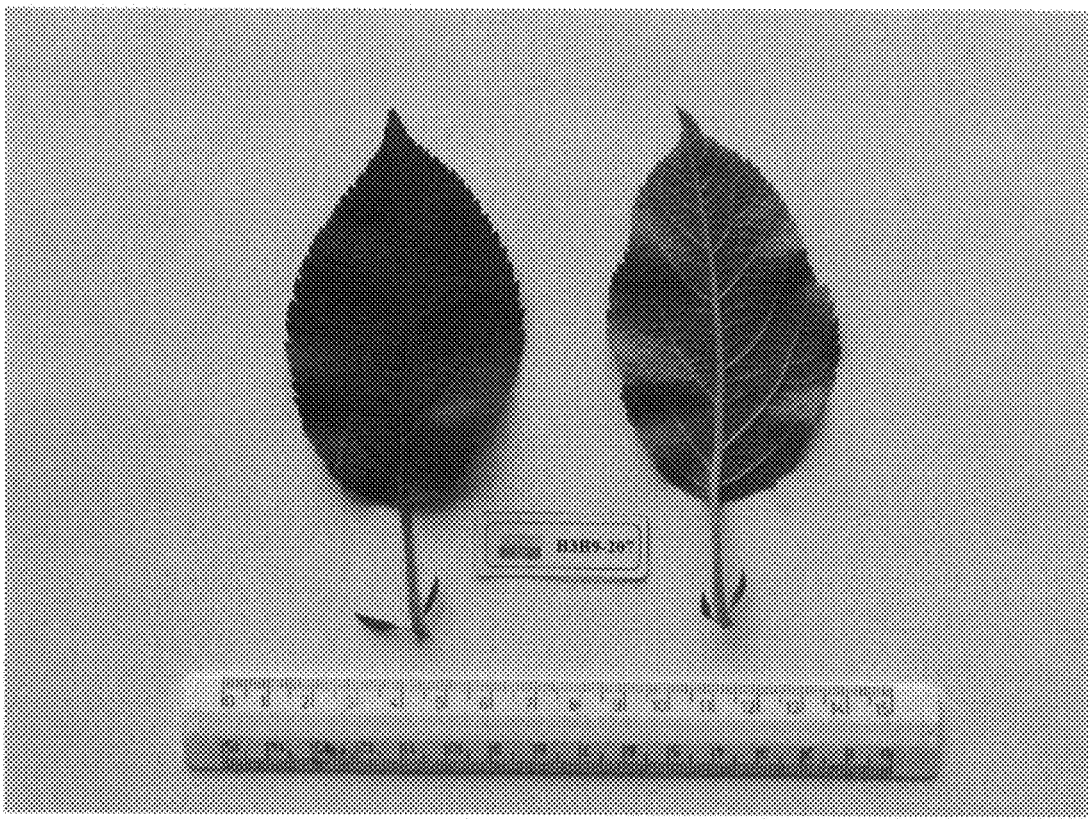
FIG. 2: illustrates the leaves of 'RENOIRCIV'.
Figure 3:
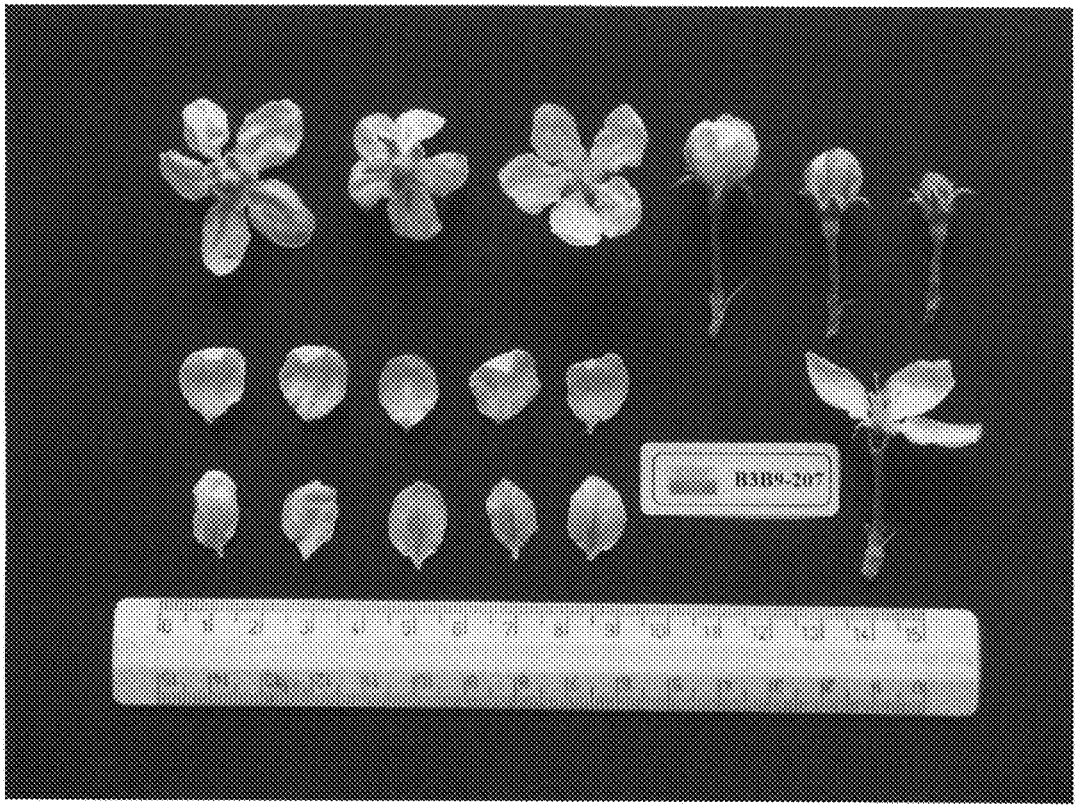
FIG. 3: illustrates the flowers of 'RENOIRCIV
Figure 4:
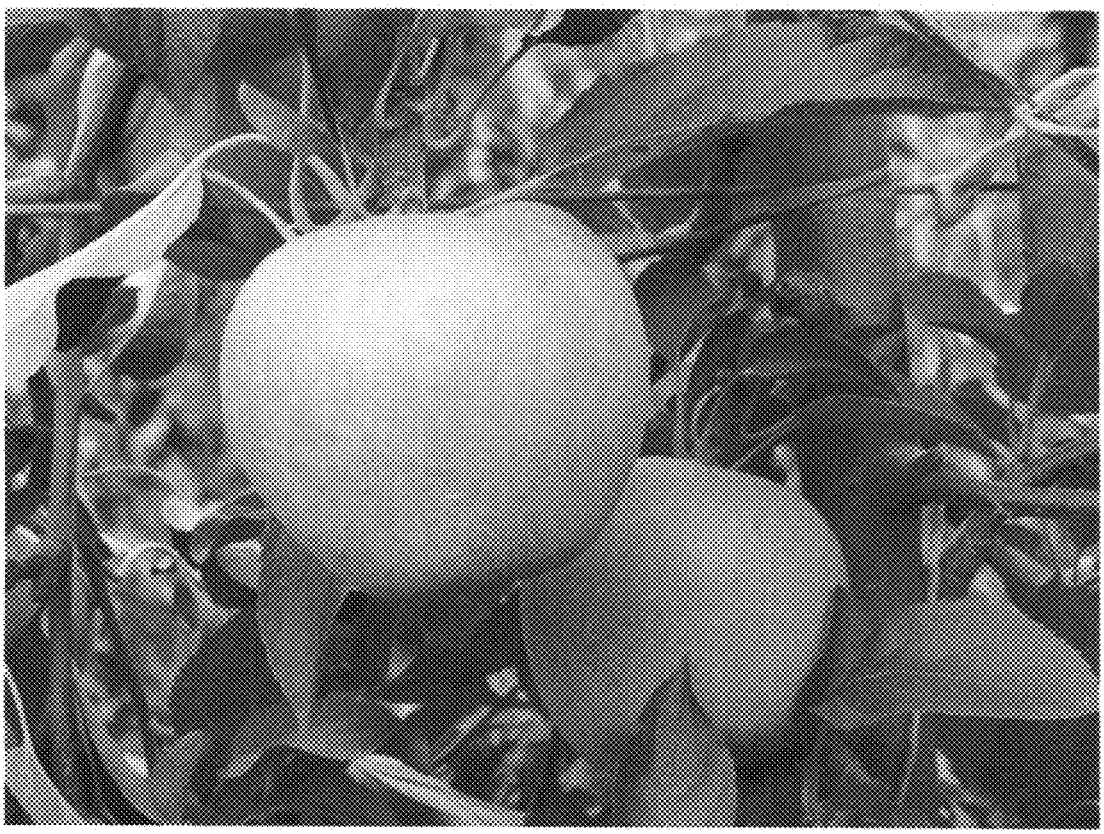
' and
FIG. 4: illustrates the fruits of 'RENOIRCIV'.

The new *Malus* variety 'RENOIRCIV' has not been observed under all possible environmental conditions. The phenotype of the new variety may vary with variations in environment such as temperature, light intensity, and day length without any change in the genotype of the plant.

The aforementioned photographs, together with the following observations, measurements and values describe the new *Malus* variety 'RENOIRCIV' as grown in the apple farm in S. Giuseppe di Comacchio (Ferrara), Italy, under conditions which closely approximate those generally used in commercial practice. The apple farm where 'RENOIRCIV' is grown is situated near the Adriatic sea (44°45' North, 12°11' East) and is zero (0) meters above sea level. The soil of the apple farm where 'RENOIRCIV' is grown is sandy, and the soil is treated with manure every year and irrigated with drip irrigation systems. The climate is temperate continental with high summer temperatures and low winter temperatures.

Unless otherwise stated, the detailed botanical description includes observations, measurements and values based on four (4) year old 'RENOIRCIV' trees that were grown in the apple farm in S. Giuseppe di Comacchio (Ferrara), Italy, from 2007 to 2010 All trees were of cropping maturity. Quantified measurements are expressed as an average of measurements taken from a number of individual trees of 'RENOIRCIV'. The measurements of any individual tree, or any group of trees, of the new variety may vary from the stated average.

Color references are made to The Royal Horticultural Society Colour Chart (R.H.S.), first publication (1966), except where general colors of ordinary significance are used. Color values were taken under daylight conditions at approximately at 10:00 am in S. Giuseppe di Comacchio (Ferrara), Italy.

All trees of 'RENOIRCIV', insofar as they have been observed, have been identical in all the characteristics described below.

Classification:

*Botanical.—Malus domestica Mill.*

Parentage:

*Female parent.—Malus domestica Mill.* 'FG-88' (unpatented proprietary selection).

*Male parent.—Malus domestica Mill.* 'B9-5' (unpatented proprietary selection).

Propagation: Budding and grafting on M9 rootstock.

Tree:

*Age.*—Observed plants were four years old.

*Vigor.*—Medium vigor.

*Tree type.*—Ramified.

*Habit.*—Spreading, branches angle is typically 45 to 75 degrees from the vertical stem.

*Density.*—Medium density.

*Cropping behavior.*—Precocious fruit bearing with good productivity.

*Type of bearing.*—Typically long shoot; brindle with fruiting apical bud.

*Production.*—$4^{th}$ year: 16 Kg.

*Size.*—Height: 2.8 m. Spread: 1.30 m. Trunk Diameter: about 45 mm as measured 20 cm above point of grafting.

*Surface texture.*—Smooth.

*Bark color.*—Brown, RHS 199 D.

*Trunk lenticels.*—Overall Shape: round to elongated. Length: about 1.0 mm. Width: about 1.0 mm. Color: Yellow-brown RHS 164 C. Density: 2 to 3 per $cm^2$.

*Branches.*—Number per tree: about 25 at four (4) years. Length: Varies due to pyramidal shape of tree. At four (4) years, maximum of 90 cm to 110 cm; minimum of 30 cm to 50 cm. Diameter (at 3 years): About 14 mm. Surface texture: smooth. Color (at 3 years): grey, RHS 201 A. Internode length: About 2.0 cm to 5.0 cm. Internode diameter: About 12 mm in the middle of branches.

*Branches lenticels.*—Length: 1.0 mm. Width: 0.5 mm. Color: Yellow-brown, RHS 164 B. Density: About 6 per $cm^2$.

Leaves:

*Arrangement.*—Alternate, simple, petiolated.

*Lamina.*—Size: Length (4 year old): 93 mm (from $3^{rd}$ to $5^{th}$ fully expanded leaf). Width (4 year old): 50 mm (from $3^{rd}$ to $5^{th}$ fully expanded leaf).

*Length/width ratio.*—1.86. Overall Shape: elliptical. Base shape: obtuse. Apex shape: right angle. Margin: biserrate. Pubescence: absent on upper surface and weak pubescent on lower surface. Attitude in relation to shoot: upwards. Color (mature leaves): green, RHS 137 A on the upper side and 147 B underside. Color (immature leaves): green, RHS 143 A on the upper side and 138 B underside.

*Venation.*—Type: prominent pinnate venation from a midrib to the edge. Color: green, RHS 147 D.

*Petiole.*—Length: about 31 mm. Diameter: about 1.85 mm in the middle. Texture: hairy. Color: yellow-green, RHS 139 C with anthocyanin coloration.

*Stipule.*—Arrangement: adnate, grown together; small size.

*Distance of stipules from basal attachment of petiole.*—Very short. Length: about 10 mm. Width: about 2 mm.

Spur:

*Present.*—Present only occasionally on 2-3 year old shoots.

*Distance between each spur.*—

*Number of fruit per spur.*—

Flowers:

*Blooming time.*—Full bloom on April $9^{th}$ in S. Giuseppe di Comacchio (Ferrara) in year 2011.

*Blooming period.*—8 to 12 days.

*Fragrance.*—Slight.

*Type.*—Inflorescence.

*Number of flowers per inflorescence.*—5 to 6.

*Flower size.*—Diameter: about 34 mm. Flower color: Primarily white, RHS 155 D; when petals fully opened, on the undersides of petals there are shades of red-purple, RHS 70 B; in the balloon stage, red-purple, RHS 58 B.

*Fruiting buds.*—The fruiting buds are located on reproductive brindle. Shape: rounded. Length: about 7.0 mm. Width: about 5.0 mm. Color: brown, RHS 200 C with hairy surface.

*Petals.*—Arrangement: intermediate. Number per flower: typically five (5). Length: average 15.93 mm. Width: average 10.32 mm. Length/width ratio: 1.54. Overall shape: elliptic. Apex shape: obtuse. Base shape: rounded. Texture: smooth. Margin: entire. Color (upper surface): white, RHS 155 D. Color (lower surface): white, RHS 155 D with shade red-purple RHS 70 B.

*Sepals.*—Number per flower: five (5). Length: average 7.81 mm. Width: average 3.31 mm. Length/width ratio: 2.4. Overall shape: lanceolate. Apex shape: acute. Texture: hairy. Margin: entire. Color: green, RHS 138 B.

*Pedicel.*—Length: average 17.1 mm. Diameter: 2 to 3 mm. Texture: hairy. Color: green, RHS 139 C.

Fruit:

*Keeping quality.*—The fruit is good to eat fresh, even directly after harvest. It has a good shelf life.

*Maturity when described.*—Ripe for eating.

*Maturity period after full bloom.*—About 130 days in S. Giuseppe di Comacchio (Ferrara) Italy.

*Date of first and last pickings.*—About 17 August and 25 August in S. Giuseppe di Comacchio (Ferrara) Italy (North 44°45'46.2", East 012°11'31.9") in year 2011.

*General shape.*—Conic-obloid.

*Average weight.*—240.37 g.

*Fruit size.*—Average height: 72.51 mm. Average diameter (at widest point): 84.3 mm.

*Position of maximum diameter.*—Between ¾ of the height near stem end.

*Height/diameter ratio.*—0.86.

*Stem.*—Length: about 29 mm. Diameter: 2 to 2.7 mm. Color: yellow-green group, RHS 153 B.

*Stalk cavity.*—Depth: average 18.44 mm. Width: average 41.98 mm.

*Eye basin.*—Aperture of eye: fully open. Depth: average 7.44 mm. Width: average 27.28 mm. Crowning at calyx end: moderate. Position of sepals: bent. Calyx tube: funnel form.

*Skin.*—Thickness: medium. Texture: rough to the touch, with russeting over 50-60% of the surface. Bloom: absent. Greasiness: absent. Firmness (at picking time): 7.5 to 8.5 kg/$cm^2$. Overcolor color: if present, it is red RHS 44 B. Percentage of skin surface with overcolor color: the overcolor is absent or very small; it is present only on the fruit growing in direct sunlight, it may take on a light red hue on the exposed part. Pattern of overcolor: if present only solid flush. Intensity of overcolor: light. Ground color: yellow-green, RHS 153 C.

*Skin lenticels.*—The lenticels are not more evident because are russet as the skin. Shape: round. Length: about 1.0 mm. Width: about 1.0 mm. Color: greyed-yellow, RHS 161 A. Density: about 3 per $cm^2$ in the central area of the surface of fruit.

*Flesh.*—Color: yellow, RHS 11C. Texture: firm, and juicy. Aroma: intense. Eating quality: excellent with a very intense aroma similar to 'Renette Blanche du Canada', but sweeter. Sugar content (at picking time): about 15.5° Brix. Acidity/Starch (at picking time): Acidity: about 8.0 g/lt Malic acid/starch: 2.5 to 3 (Laimburg scale 1 to 5).

*Core.*—Symmetry of core: asymmetric. Distinctness of core lines: no more evident. Locules: Number (per fruit): 5 (five). Length: 12 mm. Width: 5.0 mm. Form: closed or slightly open.

Seeds:

*Number per fruit.*—6 to 15.

*Number per locule.*—About 1 to 3.

*Shape.*—Elliptic.

*Length.*—Average 7.0 mm.

*Width.*—Average 4.5 mm.

*Color.*—Brown, RHS 177 A.

Reproductive organs:

*Androecium.*—Stamens: Number per flower: about 20 (Twenty). Length: average 6.85 mm. Filament: Length: about 5.9 mm. Color: green-white, RHS 155 D. Anther: Shape: ovoid, flat in the center. Length: 1.81 mm. Diameter: 1.03 mm. Color: yellow, RHS 12

C. Pollen: Amount: abundant. Color: yellow, RHS 12 B. Requirements: the crab apple "*Malus* Evereste" is good pollinator.

*Gynoecium.*—Stigma: Shape: funnel shape with receptive surface on top. Length: 0.9 mm. Width: 0.6 mm. Color: yellow-green, RHS 144 B. Style: Number per flower: 5 (Five). Length: about 10.35 mm. Width: about 0.3 mm. Color: yellow-green, RHS 145 B. Ovary: Length: about 3.0 mm. Width: about 2.0 mm. Color: green, RHS 141C.

*Use.*—Fresh market.

*Sensitivity to disease/pests.*—Scab resistance.

*Winter hardiness.*—Tolerance to temperatures of −12° C. without observed damage to wood and buds of dormant apple trees; but open flowers and young fruitlets are killed by exposure to −3° C. to −5° C., depending on the length of exposure.

*Drought/heat tolerance.*—Good tolerance to heat, up to 40° C., growth is limited by drought periods without irrigation.

*Shipping/storage characteristics.*—Very good storability under ULO-conditions (1° C., 2% $0_2$, 2% $CO_2$) for up to six (6) months.

We claim:

1. A new and distinct *Malus domestica Mill.* apple tree variety named 'RENOIRCIV', substantially as illustrated and described herein.

* * * * *